(12) United States Patent
Pargger et al.

(10) Patent No.: US 12,186,555 B2
(45) Date of Patent: Jan. 7, 2025

(54) VENTILATION MACHINE AND METHOD OF VENTILATING A PATIENT

(71) Applicant: STIMIT AG, Nidau (CH)

(72) Inventors: Hans Pargger, Aesch (CH); Ronja Müller-Bruhn, Windisch (CH)

(73) Assignee: STIMIT AG, Nidau (CH)

( * ) Notice: Subject to any disclaimer, the term of this patent is extended or adjusted under 35 U.S.C. 154(b) by 1038 days.

(21) Appl. No.: 16/967,979

(22) PCT Filed: Feb. 6, 2019

(86) PCT No.: PCT/EP2019/052880
§ 371 (c)(1),
(2) Date: Aug. 6, 2020

(87) PCT Pub. No.: WO2019/154839
PCT Pub. Date: Aug. 15, 2019

(65) Prior Publication Data
US 2021/0361964 A1   Nov. 25, 2021

(30) Foreign Application Priority Data

Feb. 6, 2018  (CH) .................................. 00135/18
Jun. 7, 2018  (CH) .................................. 00733/18

(51) Int. Cl.
| A61N 1/36 | (2006.01) |
| A61M 16/00 | (2006.01) |
| A61M 16/20 | (2006.01) |
| A61N 1/04 | (2006.01) |

(Continued)

(52) U.S. Cl.
CPC ....... *A61N 1/3601* (2013.01); *A61M 16/0051* (2013.01); *A61M 16/024* (2017.08);
(Continued)

(58) Field of Classification Search
CPC .......... A61M 16/0009; A61M 16/0051; A61M 16/0066; A61M 16/024; A61M 16/0488;
(Continued)

(56) References Cited

U.S. PATENT DOCUMENTS 5,857,957 A    1/1999  Lin
6,152,131 A *  11/2000 Heinonen .......... A61M 16/209
                                                   128/204.23

(Continued)

FOREIGN PATENT DOCUMENTS

| EP | 0993841 A1 | 8/1999 |
| JP | 2000116784 A | 4/2000 |

OTHER PUBLICATIONS

International Search Report and Written Opinion of International Application No. PCT/EP2019/052880 issued Apr. 24, 2019.

(Continued)

*Primary Examiner* — Valerie L Woodward
(74) *Attorney, Agent, or Firm* — MEDLER FERRO WOODHOUSE & MILLS PLLC

(57) ABSTRACT

A ventilation machine is disclosed that includes a conduit interface configured to be connected to a respiratory system of a human or animal patient, an air flow generator configured to deliver air through the conduit interface into the respiratory system of the patient, a processing unit in communication with the air flow generator and configured to control the airflow generator to deliver air into the respiratory system of the patient according to a breathing scheme, and an induction device for activating a diaphragm of the patient. The induction device is in communication with the processing unit. The processing unit is configured to control the induction device to activate the diaphragm in coordination with the breathing scheme.

54 Claims, 4 Drawing Sheets

(51) Int. Cl.
*A61N 1/40* (2006.01)
*A61N 2/00* (2006.01)
*A61N 2/02* (2006.01)
*A61N 7/00* (2006.01)

(52) U.S. Cl.
CPC ........ *A61M 16/204* (2014.02); *A61M 16/205* (2014.02); *A61N 1/0456* (2013.01); *A61N 1/36017* (2013.01); *A61N 1/40* (2013.01); *A61N 2/002* (2013.01); *A61N 2/006* (2013.01); *A61N 2/02* (2013.01); *A61N 7/00* (2013.01); *A61M 2016/0027* (2013.01); *A61M 2016/0036* (2013.01); *A61M 2205/054* (2013.01); *A61M 2205/057* (2013.01); *A61M 2205/058* (2013.01); *A61M 2210/1014* (2013.01); *A61N 2007/0026* (2013.01)

(58) Field of Classification Search
CPC .............. A61M 16/204; A61M 16/205; A61M 2016/0015; A61M 2016/0027; A61M 2016/0036; A61M 2205/054; A61M 2205/057; A61M 2205/058; A61M 2210/1014; A61M 31/00; A61N 1/3601; A61N 1/0456; A61N 1/36017; A61N 1/40; A61N 2/002; A61N 2/006; A61N 2/02; A61N 7/00; A61N 7/02; A61N 2007/0026
See application file for complete search history.

(56) References Cited

U.S. PATENT DOCUMENTS

| | | | |
|---|---|---|---|
| 6,360,740 B1 * | 3/2002 | Ward | A61N 1/3601 128/202.16 |
| 2004/0193003 A1 * | 9/2004 | Mechlenburg | A61N 2/02 600/15 |
| 2007/0277826 A1 | 12/2007 | Lurie | |
| 2011/0230702 A1 | 9/2011 | Honour | |
| 2011/0288609 A1 * | 11/2011 | Tehrani | A61N 1/3601 607/42 |
| 2012/0016280 A1 | 1/2012 | Aliverti et al. | |
| 2013/0238050 A1 | 9/2013 | Simon et al. | |
| 2014/0046423 A1 | 2/2014 | Rajguru et al. | |
| 2015/0231348 A1 | 8/2015 | Lee et al. | |
| 2015/0290476 A1 | 10/2015 | Krocak et al. | |
| 2015/0314133 A1 | 11/2015 | Yamashiro | |
| 2015/0367127 A1 * | 12/2015 | Meyyappan | A61N 1/0551 607/42 |
| 2016/0310730 A1 | 10/2016 | Martins et al. | |

OTHER PUBLICATIONS

Office Action issued Aug. 9, 2022 in Japanese Patent Appl. No. 2020-565528 (with English translation).

* cited by examiner

VENTILATION MACHINE AND METHOD OF VENTILATING A PATIENT

TECHNICAL FIELD

The present invention relates to a ventilation machine and more particularly to a process of manufacturing such a ventilation machine, a method of ventilating a patient and uses of such a ventilation machine.

BACKGROUND ART

In medicine, it is often required to ventilate human or animal patients for maintaining vital functions of the patient, and typically a positive pressure mechanical ventilation approach is used for such ventilation. Thereby, it can be beneficial to activate a diaphragm of the patient for assisting ventilation. In particular, in critical care units of hospitals it is desired to activate the diaphragm of ventilated patients in order to prevent drawbacks of disuse of the diaphragm. It was shown that disuse atrophy of diaphragm muscle fibers occurs already in the first 18-60 hours of mechanical ventilation, and the muscle fiber cross-sections decreased by more than 50% in this time. Thus, it is aimed to activate the diaphragm repeatedly while the patient is given artificially ventilation such that the functioning of the diaphragm can be upheld, or to activate the diaphragm at least during the weaning period to support effective restoration of independent respiratory function.

For achieving such activation of tissues in a patient's body, it is known to directly stimulate the tissue or to indirectly activate the tissue via stimulation of specific parts of the neural system. For example, the diaphragm being a muscular tissue can be activated by providing electric pulses directly to the tissue or to nerves associated to the tissue. More specifically, it is known that the diaphragm can be activated by stimulating the Phrenic nerve, e.g., on the level of the neck of the patient.

In this context, US 2016/0310730 A1 describes an apparatus for reducing ventilation induced diaphragm disuse in a patient receiving ventilation support from a mechanical ventilator (MV). The apparatus includes an electrode array of first and second types and comprising a plurality of electrodes configured to stimulate a phrenic nerve of the patient, and at least one controller identifying a type of electrode array from at least two different types, and generating a stimulus signal for stimulating a phrenic nerve of the patient based upon the identity of the electrode type. Such electrode-based stimulation is not very robust to patient movements or relocations, and the possible stimulation depth can be significantly limited by bones or fatty tissue. Furthermore, electrode stimulation is reported to be more painful for the patient than electro-magnetic stimulation.

Therefore, there is a need for a system allowing a more convenient and efficient operation as well as less side effects in stimulation.

DISCLOSURE OF THE INVENTION

According to the invention this need is settled by a ventilation machine as it is defined by the features of a first independent claim, by a process of manufacturing a ventilation machine as it is defined by the features of a second independent claim, by a method of ventilating a patient as it is defined by the features of a third independent claim, and by a method of transcutaneous induction of a Phrenic nerve for a diagnostic purpose to assess diaphragm function, or sleep apnea, or other forms of sleep-disordered breathing, for repetitive regular transcutaneous induction of a Phrenic nerve for therapeutic use in patients with no spontaneous breath, for reanimation and keeping alive patient who have no function of a respiratory center, or for repeated transcutaneous induction of a Phrenic nerve for therapeutic use in patients with no or insufficient spontaneous diaphragm contractions who have at least a partly intact Phrenic nerve as it is defined by the features of a fourth independent claim. Preferred embodiments are subject of the dependent claims.

In one aspect, the invention is a ventilation machine comprising a conduit interface, an air flow generator, a processing unit and an induction device. The conduit interface is configured to be connected to a respiratory system of a human or animal patient. The air flow generator is configured to deliver air through the conduit interface into the respiratory system of the patient. The processing unit is in communication with the air flow generator and is configured to control the airflow generator to deliver air into the respiratory system of the patient according to a breathing scheme. The induction device is embodied to activate a diaphragm of the patient. The induction device is in communication with the processing unit and the processing unit is configured to control the induction device to activate the diaphragm in coordination with the breathing scheme.

The term "in communication" as used in connection with the processing unit and the air flow generator and the induction device can relate to any connection of elements allowing to communicate such as to transfer or exchange information or data. The elements can be in communication by being in wired or wireless connection with each other. They can comprise respective adapters or the like. Elements can also be in communication by indirectly communicating or being synchronized. For example, they can be triggered by a correlating event such as by a diaphragm activity feedback signal from a sensor or by a regular time trigger.

The term "breathing scheme" relates to a sequence of inhalations and exhalations over time. It can be continuous such that it comprises the same rhythm of inhalations, exhalations and breaks in between. Or it can be adaptive such that variations in the in-/exhalation rhythm and intensity occur. The breathing scheme can also comprise operations of the air flow generator and/or the induction device. In particular, it can comprise sequences of the air flow generator delivering air to the patient and intermissions in between. It can further comprise sequences of the induction device stimulating the diaphragm and intermissions in between. All the sequences or some of the sequences can be synchronized.

The term "synchronize" in this connection can relate to many ways of synchronizing, and is not limited to exact timely synchronization of two activities. For example, two activities may be started or ended with a positive or negative time shift between them or within a time window.

The breathing scheme can define various variants of inducing ventilation of the patient. For example, it can define that in each cycle the induction device is operated for a specific time and that the air flow generator is added a predefined time gap after operation of the induction device has started. For this, the breathing scheme preferably comprises a time gap between start of operation of the induction device and start of operation of the air flow generator. Like this, inhalation can be initiated first by the induction device and then later be assisted by the air flow generator. When the ventilation machine is equipped with one or more sensor members as described in more detail below, a trigger event detected by the sensor member can be defined in the breathing scheme. For example, such trigger event can be the detection of a spontaneous diaphragm activation or a spontaneous inhalation by the patient. The breathing scheme can then define that the induction device stimulation starts when the trigger event is detected. Advantageously, a form of direct diaphragm activation feedback is used for such trigger. Operation of the air flow generator can be started a predefined time gap after starting operation of the induction device. Or, it can start upon detection of a further trigger event. Such further trigger event can be a sensor member detecting that a specific inhalation volume, flow or pressure is achieved or not achieved. Or, it can be the detection of a specific oxygen pressure value ($pO_2$) or carbondioxide pressure value ($pCO_2$) in the blood or any other suitable measurement. In any variant, the ventilation machine can apply a continuous base air pressure for assisting breathing, e.g. positive endexspiratory pressure (PEEP). Such base pressure can also be defined in the breathing scheme.

The breathing scheme can be initially calibrated by pretesting the breathing activity of the patient. In particular, such calibration can exclude or include any active air flow provision but certainly exclude stimulation of the diaphragm. Like this, an appropriate or ideal volume and/or flow and/or pressure and/or $pO_2$ and/or $pCO_2$ pattern can be determined. This pattern can also be referred to as "ideal pattern". It can be aimed to be reproduced by operating the ventilation machine including stimulation of the diaphragm.

Calibration of the breathing scheme can be as follows: (i) Initially, when the patient arrives, the patient is mechanically ventilated as per standard procedures. Mechanical air flow generator settings are adjusted to achieve sufficient ventilation and oxygenation. (ii) During this phase, the personnel or the sensor member monitors, how much minute ventilation/tidal volume (TV)/flow over time (Integral)/total pressure is produced by (ii-1) the patient himself (spontaneous breathing without ventilator support), (ii-2) the air flow generator, and/or (ii-3) the sum of both which can be the target value or ideal pattern. (iii) Stimulate Phrenic nerve in a window of minimum flow which typically is towards the end of the exhalation phase before inhalation starts, and identify optimum stimulator settings such as patient individual frequency-intensity combination and stimulator positioning producing tidal volume over inhalation time. (iv) Measure diaphragm activity via a sensor member such as measure TV/flow/other sensor signals. (v) Operate air flow generator and induction device in synchrony with a low air flow supply initially, and add extra flow/volume/pressure by the air flow generator until the target value or ideal pattern or a selectable/adjustable fraction thereof is reached. If no significant air flow supply is needed, the mechanical ventilator can run in as back-up mode to support ventilation only in events or periods, when the "ideal pattern" is lost/not achieved, or the mechanical ventilator can supply a PEEP pressure only.

The induction device can be embodied to activate the diaphragm or midriff of the patient directly or via the neural system. The neural system can comprise or be a single or a plurality of nerves such as, particularly, the Phrenic nerve. Thereby, in many applications it is advantageous to repeatedly stimulate the neural system or the nerves and particularly the Phrenic nerve.

The processing unit can be embodied or configured by having an appropriate software running on a computing device. It can be a single entity or a composition of distributed components. For example, the processing unit can be a computing device external to the air flow generator and/or the induction device but connected to them. Or, it can be embodied in the air flow generator and/or the induction device and combined to perform the required functions. Or, it can be a combination of an external computing device and components of the air flow generator and/or the induction device.

The ventilation machine allows for coordinating the activation of the diaphragm via the Phrenic nerve within ventilating the patient. Particularly, when manually or regularly activating the diaphragm during ventilation as known in the art, often the problem occurs that the diaphragm is activated at a wrong time, such as when providing air into the respiratory system. The ventilation machine described herein allows for defining a breathing scheme and to coordinate ventilation and activation of the diaphragm by using the induction device for stimulating the Phrenic nerve in an accurate and efficient manner.

The ventilation machine can also be operated in a backup mode. In such a mode the spontaneous breathing of the patient is monitored and the ventilation machine assists breathing in case a deviation between the breathing of the patient and a predefined target breathing or the breathing scheme is detected.

In particular, the ventilation machine preferably comprising a breathing activity sensor arranged to sense breathing of the patient (spontaneous breathing and/or artificial breathing induced by the device), wherein the processing unit is configured to control the airflow generator to deliver air into the respiratory system of the patient according to a breathing scheme upon the breathing activity sensor failing to sense sufficient breathing of the patient, and optionally to control the induction device to activate the diaphragm in coordination with the breathing scheme upon the breathing activity sensor failing to sense sufficient breathing of the patient. The breathing activity sensor can be the sensor member of the ventilation machine or any other means allowing to sense or detect sufficient breathing of the patient or indirect related effects (e.g. oxygeneation). The term "sufficient breathing" as used herein can relate to a breathing or spontaneous breathing allowing to provide for an oxygen supply to the patient appropriate to maintain vital and other functions of the patient's body.

Preferably, the processing unit comprises an input interface and is configured such that the breathing scheme can be inputted via the input interface. The input interface can comprise a bus or an adapter via which data representing the breathing scheme can be provided to the processing unit. Or, it can comprise a keyboard and/or mouse and/or touch screen allowing a user to define the breathing scheme in the processing unit. Advantageously, the processing unit is also equipped with a screen or another peripheral device allowing to present information to a user. By having such input interface, the processing unit allows for efficiently defining the breathing scheme suitable for the particular patient.

The processing unit preferably is configured to control the air flow generator to deliver air through the conduit interface into the respiratory system of the patient by applying cycles of forwarding air into the respiratory system of the patient and allowing exhalation of air from the respiratory system in accordance with the breathing scheme. Allowing exhalation of the air from the respiratory system advantageously happens passively by reducing the pressure in the conduit interface and particularly without applying an underpressure. Thereby, the air flow generator receives air through the conduit interface. Such cycles allow for achieving a repetitive and continuous ventilation or assisted breathing of the patient. Thereby, the processing unit preferably is configured to control the induction device to activate the diaphragm between the cycles of the breathing scheme. By activating the diaphragm, the body of the patient can start breathing or inhaling without air being pressed into the respiratory system by the air flow generator. Like this, spontaneous breathing can be initiated or supported.

The processing unit preferably is configured to control the induction device to activate the diaphragm right before each start of one of the cycles of the breathing scheme. The term "right before" in this connection relates to a well defined delay or time before the start of the respective cycle of the breathing scheme. Thereby, the delay can be predefined in the system. Alternatively, the processing unit can be configured to allow the user to set the delay, e.g. via the input interface. An appropriate delay can be in a range of 0 seconds to 1 second.

Preferably, the processing unit is configured to control the induction device to activate the diaphragm in synchrony with inhalation cycles of the breathing scheme.

Preferably, the air flow generator comprises an inspiration valve configured to allow delivery of air through the conduit interface into the respiratory system of the patient, and an expiration valve configured to allow patient exhalation, wherein, in accordance with the breathing scheme, the inspiration valve is synchronized with the activity of the induction device and the expiration valve is synchronized with inactivity of the induction device.

In an advantageous embodiment, the ventilation machine comprises a sensor for detecting a trigger event. Such trigger event can, e.g., be an activation of the diaphragm which is not sufficient for spontaneous breathing. The processing unit can be configured to activate the diaphragm once a trigger event is detected by operating the induction device. The active or mechanical ventilation can then start with predefined or user defined delay after operation of the induction device started. In another advantageous embodiment, the processing unit is configured to start operation of the induction device with a well defined delay or a user-selected delay before the air flow generator provides air into the patient.

The induction device can be any device suitable for directly or indirectly stimulating or activating the diaphragm. For example, the induction device can be embodied to magnetically stimulating the diaphragm or a Phrenic nerve. Preferably, the induction device comprises at least one electrode configured to activate the diaphragm by stimulating a Phrenic nerve under control of the processing unit. Such an electrode allows indirect activation of the diaphragm by comparably simple and reliable means.

In a preferred embodiment, the induction device is an electro-magnetic or magnetic induction device. Preferably, the induction device comprises an electro-magnetic field generator with a coil design configured to generate a spatial electro-magnetic field having a targeted shape. The electro-magnetic field generator can also be referred to as electro-magnetic field creator. The targeted shape can be achieved by the electro-magnetic field being a locally constrained, targeted electric field, e.g., having a peak. The coil design can be or comprise at least two coils, at least one cone shaped coil, at least one parabolic coil or at least one other curved or bulged coil. The targeted shape can be adapted to be active in a target area being the nerve area that shall be activated with the electromagnetic-field, which can be for example achieved by the peak in the electro-magnetic field (focality area). The time dependence and spatial distribution of the electro-magnetic field and the field strength can be tuned in such a way that the desired activation of the target area is achieved. The coil design of the electro-magnetic field generator allows to shape or customize the electro-magnetic field in compliance with the intended application of the ventilation device. In particular, the targeted shape can be created such that it is comparably sharp. This allows for specifically stimulating the neural system or a specific portion thereof. In particular, it allows for specifically stimulating a nerve such as the Phrenic nerve and for lowering or preventing stimulation of other tissue or nerves neighboring, surrounding or overheading the targeted nerve. The process of localizing the target nerve can also be supported by ultrasound imaging techniques. In addition, a second feedback mechanism may be implemented. In order to stimulate both Phrenic nerves at a neck, the coil design can be provided which is characterized by a double coil generating focal e-field area(s), a parabolic coil or a small circular coil.

Thereby, the induction device preferably is configured to activate the diaphragm by the spatial electro-magnetic field stimulating a Phrenic nerve under control of the processing unit. Such arrangement in which the processing unit controls the activation of the diaphragm by operating the induction device having the electro-magnetic field generator allows for precisely stimulating the Phrenic nerve. In particular, the coil design can allow for a high accuracy and specificity of the electro-magnetic field which can be accurately controlled by the processing unit.

Alternatively or additionally, the induction device preferably comprises a focused ultrasound device to activate the diaphragm by transcutaneously stimulating a Phrenic nerve under control of the processing unit. The induction device preferably comprises at least one electrode, such as a needle electrode, configured to activate the diaphragm percutaneously.

Preferably, the processing unit is configured to stop activity of the induction device in synchrony with the end of each inhalation phase of the breathing cycles. In particular, such stops can be implemented always when the air flow generator switches into an exhalation mode or opens the exhalation valve.

Preferably, the ventilation machine comprises a sensor member configured to detect an activation or activity of the diaphragm. Such sensor member allows for gathering a trigger event which can be used in the breathing scheme as described above. The sensor member can comprise at least one electrode configured to be attached to the human or animal body such that it senses an activity of the diaphragm. Such an electrode can efficiently detect activation of the diaphragm such that the induced activation and/or spontaneous activity can be monitored. Alternatively, the activity of the diaphragm can be monitored by other direct means such as an oesophagus catheter, a myogram or the like. Or, it can be monitored by indirect means such as effects of the diaphragm activity on the flows pattern of a flow sensor, on the pressure patterns of a pressure sensor, on strain gauges or acceleration sensor detecting movements of the chest, or the like. Additionally or alternatively, the sensor member preferably comprises accelerators and/or gyroscopes and/or strain gauges, on the chest of the patient to detect diaphragm contractions.

Also, an oesophagus catheter or other types of catheters may be used as a sensor member to detect activation of the diaphragm. A catheter to measure compound muscle action potentials (CMAP) of diaphragm may be used as a sensor member. A catheter in esophagus that measures the electrical activity of the diaphragm may be used as a sensor member. EMG measurement of diaphragm using catheter may be used. A transdiaphragmatic pressure sensor as catheter may be used as a sensor member, measuring gastric pressure (Pga) and esophagus pressure (Pes), sensor type: balloon catheter and pressure transducer. This requires the placement of small balloon-tipped catheters into the esophagus and stomach to assess intrathoracic and intra-abdominal pressures, respectively. Or, ultrasound monitoring may be used as a sensor member to detect diaphragm activations. Further, oxymetry measures may be used as indicators about inhalation activities/diaphragm activation. Also elastic bands or belts (around chest or other expanding structures) may be used as sensor member to detect diaphragm activations; cross-section changes in bands or belts can serve as indicators for muscle or diaphragm contractions. Electrodes on target muscles or diaphragm to measure action potentials (e.g. electroenzephalograms) can be used as a sensor member to detect diaphragm activation. For example, cutaneous EMG measurement of diaphragm may be used as sensor member, whereby diaphragmatic EMG is monitored with a surface electrode positioned between the seventh and ninth intercostal spaces in the anterior axillary line. Mechanical stretch sensors on skin measuring thorax deformation may be used as a sensor member. Electrical impedance tomography, e.g. in form of a belt measuring lung volume, may be used as a sensor member.

Myograms, oesophagus catheters, chest electrodes, diaphragm EMGs are typically considered as "direct" diaphragm activation measurement devices, whereby flow sensors will be considered "indirect" diaphragm activation measurement devices. All other measurement devices may be considered as "direct" or "indirect" diaphragm activation measurement devices, depending on the speed (time delay) of detection of diaphragm activity.

Additionally or alternatively, the sensor member can comprises a flow sensor having an adaptor connectable to a respiratory system of the human or animal body, the flow sensor being configured to detect an air flow change induced by an activity of the diaphragm. The term "flow sensor" as used herein relates to any device allowing for detecting an air movement and, in particular, change of the air movement resulting in a pressure change. Typically, flow sensors measure the number of times a fixed volume is filled by the fluid within a specific time frame, a force or pressure produced in the flowing stream of the fluid or a velocity of the fluid over a known area. The adaptor can particularly be configured to be connected to an airway of the respiratory system. The flow sensor can be integral with the induction device or air flow generator, e.g. in one unit. It can also be comprised in another unit such as an associated ventilation machine or the like. Thereby, the adaptor of the flow sensor of the sensor member can be configured to be connected to a mouth and/or a nose and/or trachea of the human or animal body. The term "connected" as used herein relates to any direct connection or indirect connection via another element. For example, the adaptor can be indirectly connected to the mouth and/or nose via a tube and/or trachea.

Preferably, the sensor member is configured to trigger the induction device and the air flow generator. Such triggering allows for efficiently activating and/or deactivating the induction device and the air flow generator in accordance with the breathing scheme. Also separate sensor members can be provided, one for triggering the induction device and one for triggering the air flow generator.

The processing unit preferably is configured to activate the induction device and the air flow generator with an adjustable time gap or time delay towards the trigger from the sensor member. Like this, the temporal relationship between operation of the induction device and the air flow generator towards the trigger can efficiently be set.

The processing unit preferably is configured to trigger the induction device upon a signal characteristic of the sensor member measuring diaphragm activation, such as a myogram or a oesophagus catheter, and to trigger the air flow generator upon a signal characteristic from the sensor member measuring indirect diaphragm activation, such as a flow and/or pressure change.

Preferably, the processing unit is configured to automatically vary plural breathing scheme parameters such as adjustable time gaps and/or field strength of the spatial electro-magnetic field and/or ramp duration of the spatial electro-magnetic field and/or overall air flow duration and/or flow field strengths and/or expiration phase duration and/or temporal characteristics of the electro-magnetic field. Like this, the ideal pattern can be achieved. Or an optimal target value or target value range such as a value inside a range of $pO_2$ or $pCO_2$ as inputted by an operator can be achieved.

The processing unit can be configured to activate only the induction device in regular time intervals or in accordance to the breathing scheme; to inactivate the air flow generator or operate it in a PEEP mode; to activate the air flow generator to contribute to the breathing scheme only when the actual pattern is too far away from the ideal pattern or other out of the target value/target value range such as, e.g., $pO_2$ value too low/$pCO_2$ value too high.

In a preferred embodiment, the ventilation machine comprises a calibration unit, wherein the induction device comprises an electro-magnetic field adjustment mechanism configured to automatically adjust the position of the spatial electro-magnetic field generated by the coil design, the processing unit is in communication with the sensor member of the induction device and with the electro-magnetic field adjustment mechanism of the induction device, the processing unit is configured to control the electro-magnetic field adjustment mechanism of the induction device to automatically vary the position of the spatial electro-magnetic field generated by the coil design of the induction device, the processing unit is configured to receive an activation feedback signal from the sensor member of the induction device upon detection of the activation of the diaphragm, and the processing unit is configured to control the electro-magnetic field adjustment mechanism of the induction device to automatically stop variation of the position of the spatial electro-magnetic field generated by the coil design of the induction device.

Preferably, the electro-magnetic field adjustment mechanism is configured to automatically adjust a field strength of the electro-magnetic field generated by the coil design, the processing unit is configured to control the electro-magnetic field adjustment mechanism of the induction device to automatically vary the field strength of the electro-magnetic field generated by the coil design of the induction device, and the processing unit is configured to control the electro-magnetic field adjustment mechanism of the induction device to automatically stop variation of the field strength of the electro-magnetic field generated by the coil design of the induction device.

By such calibration unit, the electro-magnetic field generator can automatically be orientated and adjusted, i.e. calibrated, such that the neural system is stimulated to specifically activate the diaphragm or diaphragm. In particular, the strength of the electro-magnetic field created and the orientation of its targeted shape can be automatically varied until the neural system is stimulated such that the sensor receives a signal of the diaphragm being activated. In that configuration, the neural system is specifically stimulated and due to the spatial electro-magnetic field the side effects such as stimulation of other portions of the neural system can be lowered or minimized. Moreover, the system could react to patient movements, and automatically re-orient towards the new location of the target nerve. Thereby, the calibration unit, the electro-magnetic field adjustment mechanism and the sensor member can form an automated feedback system implemented in the electro-magnetic induction device.

Like this, the electro-magnetic induction device of the ventilation machine allows for an automatic, convenient and efficient operation and, more particular, for a simple, precise and specific localization of the portion of the neural system to be stimulated for activating the diaphragm. By automatically calibrating the device, a considerable higher accuracy can be achieved compared to a manual localization of the relevant portion of the neural system, and usability can be improved. Additionally, the device allows for reducing the side effects in stimulation of the neural system.

The electro-magnetic field can be generated by the electro-magnetic field generator in single pulses or as a train. Thereby, single pulses relate to the generation of the electro-magnetic filed over a comparably short time and with a comparably long interruption between two subsequent pulses. Typically, single pulses are provided at frequencies lower than 10 Hz, or initiated manually by a user. Such pulses can activate nerves and muscles and are identifiable by the patient. In particular, such single pulses may cause a single convulsion of a muscle. In contrast thereto, when being generated in a train, the electro-magnetic field is generated in sequences of pulses comparably quickly following each other. Such pulses can be provided at a frequency in a range of in between about 15 Hz and about 30 Hz. In particular, a train may achieve to activate a nerve or muscle such that a continuous contraction or activation is induced. Advantageously, the train is provided by increasing the intensity and/or frequency until a target intensity and frequency is achieved ("ramp protocol"). Like this, sudden convulsion, patient surprise, sudden patient startling or discomfort can be decreased.

The induction device preferably comprises a mounting arrangement holding the coil design of the electro-magnetic field generator, the mounting arrangement being configured to hold the coil design of the electro-magnetic field generator at the patient. The mounting arrangement can be embodied to hold the coil design of the electro-magnetic field generator in a specific target position at the human or animal body. In particular, such target position may be a position in which a targeted portion of the neural system can be reached by the electro-magnetic field created by the coils. The term "holding at" as used in connection with the mounting arrangement can relate to the coil design being in contact with the body or in close distance to it. The position and orientation of the coil design can thereby be predefined or distinct. Such mounting arrangement allows for efficiently and precisely positioning the induction device, and eventually its coil design, such that the diaphragm can efficiently be activated.

The mounting arrangement can comprise a repositioning structure configured to automatically change a position of the coil design of the electro-magnetic field generator relative to the human or animal body when being held at the human or animal body. The term "position" as used in connection with the automatic changing by the repositioning structure can relate to a location, orientation, form-shaping or the like and combinations thereof. The position can be changed by tilting, shifting, relocating, reshaping or similar actions. Like this, the orientation of the spatial electro-magnetic field can efficiently and precisely be adjusted.

Thereby, the electro-magnetic field adjustment mechanism can comprise the repositioning structure of the mounting arrangement and the calibration unit can be configured to automatically vary the position of the spatial electro-magnetic field by inducing the repositioning structure to automatically change the position of the coil design relative to the human or animal body. The repositioning structure of the mounting arrangement can comprise a joint configured to tilt the coil design of the electro-magnetic field generator relative to the human or animal body when being held at the human or animal body. This allows for an efficient adaptation of the position and/or orientation to adjust the spatial electro-magnetic field in order to stimulate the neural system.

The mounting arrangement can be configured to hold the coil design at the neck of the human or animal body such that a Phrenic nerve of the neural system of the human or animal body can be reached by the spatial electro-magnetic field generated by the coil design of the electro-magnetic field generator. Such an embodiment allows for efficiently stimulating the Phrenic nerve and to activate the diaphragm.

Alternatively or additionally, the electro-magnetic field generator can comprise a repositionable conductive element located in the electro-magnetic field generated by the coil design. Such a conductive element allows for an alternative efficient adjustment of the spatial electro-magnetic field. Thereby, the electro-magnetic field adjustment mechanism can comprise the conductive element of the electro-magnetic field generator and the calibration unit can be configured to automatically vary the position of the spatial electro-magnetic field by inducing the electro-magnetic field adjustment mechanism to automatically reposition the conductive element in the electro-magnetic field. The conductive element can comprise a conductive shaft. Such a shaft may be an simple and efficient embodiments for precisely adjust the spatial electro-magnetic field. In this context the term "shaft" may relate to any suitable rod-like structure such as a bar, a pole, a stick, a stem, a post or the like.

The electro-magnetic field generator can comprise an array of coils including the coil design. In particular, the array can consist of three or more coils. Such array allows for more sophisticatedly shape and move the electro-magnetic field and particularly its targeted shape. Thereby, the electro-magnetic field adjustment mechanism can comprise the array of coils of the electro-magnetic field generator and the calibration unit preferably is configured to automatically vary the position of the spatial electro-magnetic field by inducing the electro-magnetic field adjustment mechanism to automatically empower different coil combinations of the array of coils. The coils of the array of coils can overlap. The array of coils of the electro-magnetic field generator preferably are arranged to generate a plurality of electro-magnetic fields each having a targeted shape, the array of coils being arranged such that the plurality of electro-magnetic fields overlap and generate an accumulated intensity. With such accumulated intensity, a more precise and well defined targeted electric field can be generated such that the neural system can be precisely stimulated.

In a preferred embodiment, the sensor member of the ventilation machine comprises a flow sensor connected to the conduit interface and configured to detect an air flow change induced by an activity of the diaphragm. Thereby, the flow sensor of the sensor member preferably is integral with the conduit interface. Such flow sensor allows for efficiently detecting a breathing activity of the patient or a breathing induced by the induction device and/or the air flow generator. Thus, the flow sensor allows for efficiently providing a feedback corresponding to any breathing of the patient.

Preferably, the ventilation machine is a single assembly. Such single assembly allows for efficiently adapting the components of the machine such that they match to each other and such that they efficiently interact.

Preferably, the sensor member comprises a pressure sensor having an adaptor connectable to a respiratory system of the human or animal body, the pressure sensor being configured to detect a pressure change induced by an activity of the diaphragm. The adaptor of the pressure sensor of the sensor member can be configured to be connected to a mouth and/or a nose of the human or animal body. The pressure sensor can be integral with the induction device, e.g. in one unit. It can also be comprised in another unit such as an associated ventilation machine or the like.

In one preferred embodiment, the ventilation machine according to the invention is used for induction of a Phrenic nerve for a diagnostic purpose to assess diaphragm function, or sleep apnoa, or other forms of sleep-disordered breathing.

In another preferred embodiment, the ventilation machine according to the invention is used for repetitive regular induction of a Phrenic nerve for therapeutic use in patients with no spontaneous breath, for example for reanimation and keeping alive patients who have no function of a respiratory center, e.g. sedated patients, intensive care patients or anaesthetized patients. The repetitive regular induction can be in particular ten to fifty stimuli per minute. The no function of the respiratory center can result from drugs or opioid consumption. The use can be involved in an immediate therapy for patients with missing stimulus due to interrupted connection between respiratory center and diaphragm such as, e.g., paraplegic patients after accidents, for use in patients with missing stimulus due to sedation or respiratory depression, or for use in mechanically ventilated patients without trigger.

In a further other preferred embodiment, the ventilation machine according to the invention is used for repeated transcutanous induction of a Phrenic nerve for therapeutic use in patients with no or insufficient spontaneous diaphragm contractions who have at least a partly intact Phrenic nerve. These therapeutic applications may include for example to treat or avoid diaphragm weakness in mechanically ventilated patients, to avoid or treat lung infections in mechanically ventilated patients, for use in COPD patients, for reanimation and keeping alive patients who have impaired function of the respiratory center (e.g. from drugs or opeoids), for treatment of sleep apnoa and other forms of sleep-disordered breathing; to treat patients with idiopathic diaphragm paralysis, neuralgic amyotrophy or ALS, to treat hypercapnia.

In another aspect, the invention is a process of manufacturing a ventilation machine. This process comprises assembling the following to the ventilation machine: (i) a conduit interface configured to be connected to a respiratory system of a human or animal patient; (ii) an air flow generator configured to deliver air through the conduit interface into the respiratory system of the patient; (iii) a processing unit in communication with the air flow generator and configured to control the airflow generator to deliver air into the respiratory system of the patient according to a breathing scheme; and (iv) an induction device for activating a diaphragm of the patient to the ventilation machine, wherein the induction device is in communication with the processing unit. The manufacturing process further comprises a step of configuring the processing unit to control the induction device to activate the diaphragm in coordination with the breathing scheme. The breathing scheme preferably comprises a time gap between start of operation of the induction device and start of operation of the air flow generator.

The process according the invention allows for efficiently manufacturing the ventilation machine according to the invention as well as its preferred embodiments. Thereby, the effects and benefits described above in connection with the ventilation machine according to the invention and its preferred embodiments can be achieved.

In the following further preferred steps and characteristics of the manufacturing process according to the invention are listed.

Preferably, the process comprises a step of providing the processing unit with an input interface and the processing unit is configured such that the breathing scheme can be inputted via the input interface.

The process preferably comprises a step of configuring the air flow generator to deliver air through the conduit interface into the respiratory system of the patient by applying cycles of forwarding air into the respiratory system of the patient and allowing exhalation air from the respiratory system in accordance with the breathing scheme.

Preferably, the process comprises a step of configuring the processing unit to control the induction device to activate the diaphragm in synchrony with inhalation cycles of the breathing scheme.

The air flow generator preferably comprises an inspiration valve configured to allow delivery of air through the conduit interface into the respiratory system of the patient, and an expiration valve configured to allow patient exhalation, wherein, in accordance with the breathing scheme, the inspiration valve is synchronized with the activity of the induction device and the expiration valve is synchronized with inactivity of the induction device.

Thereby, the processing unit preferably is configured to control the induction device to activate the diaphragm between the cycles of the breathing scheme.

Further, the process preferably comprises as step of configuring the processing unit to control the induction device to activate the diaphragm right before each start of one of the cycles of the breathing scheme.

Preferably, the process comprises a step of providing the induction device with at least one electrode configured to activate the diaphragm by transcutaneously stimulating a Phrenic nerve under control of the processing unit.

Preferably, the process comprises a step of providing the induction device with an electro-magnetic field generator with a coil design configured to generate a spatial electro-magnetic field having a targeted shape. Thereby, the induction device preferably is configured to activate the diaphragm by the spatial electro-magnetic field stimulating a Phrenic nerve under control of the processing unit.

The process preferably comprises a step of providing the induction device with a mounting arrangement holding the coil design of the electro-magnetic field generator, the mounting arrangement being configured to hold the coil design of the electro-magnetic field generator at the patient.

The process preferably comprises a step of configuring the processing unit to stop activity of the induction device in synchrony with the end of each inhalation phase of the breathing cycles.

Preferably, the manufacturing process comprises a step of providing the ventilation machine with a sensor member configured to detect an activation of the diaphragm.

Thereby, the process preferably comprises a step of configuring the sensor member to trigger the induction device and the air flow generator.

Preferably, the process comprises a step of configuring the processing unit to activate the induction device and the air flow generator with an adjustable time gap towards the trigger from the sensor member.

The process preferably comprises a step of configuring the processing unit to trigger the induction device upon a signal characteristic of the sensor member measuring diaphragm activation and to trigger the air flow generator upon a signal characteristic from the sensor member measuring indirect diaphragm activation.

Preferably, the process comprises a step of configuring the processing unit (3; 30; 38) to automatically vary plural breathing scheme parameters and/or field strength of the spatial electro-magnetic field and/or ramp duration of the spatial electro-magnetic field and/or overall air flow duration and/or flow field strengths and/or expiration phase duration and/or temporal characteristics of the electro-magnetic field.

Further, the ventilation machine preferably is provided with a calibration unit, wherein (i) the induction device is provided with an electro-magnetic field adjustment mechanism configured to automatically adjust the position of the spatial electro-magnetic field generated by the coil design and to automatically adjust a field strength of the electro-magnetic field generated by the coil design; (ii) the processing unit is in communication with the sensor member of the induction device and with the electro-magnetic field adjustment mechanism of the induction device; the processing unit is configured to control the electro-magnetic field adjustment mechanism of the induction device to automatically vary the position of the spatial electro-magnetic field generated by the coil design of the induction device and to automatically vary the field strength of the electro-magnetic field generated by the coil design of the induction device; (iii) the processing unit is configured to receive an activation feedback signal from the sensor member of the induction device upon detection of the activation of the diaphragm; and (iv) the processing unit is configured to control the electro-magnetic field adjustment mechanism of the induction device to automatically stop variation of the position of the spatial electro-magnetic field generated by the coil design of the induction device and to automatically stop variation of the field strength of the electro-magnetic field generated by the coil design of the induction device.

The sensor member preferably is provided with a flow sensor connected to the conduit interface and configured to detect an air flow change induced by an activity of the diaphragm. Thereby, the flow sensor of the sensor member preferably is integral with the conduit interface.

The ventilation machine preferably is embodied as a single piece assembly.

Preferably, the process comprises a step of assembling an alarm unit into the induction device, wherein the tracker is connected to the alarm unit and configured to activate the alarm unit when the detected movement exceeds a range of compensation achievable by changing the position of the spatial electro-magnetic field generated by the two coils via the electro-magnetic field adjustment mechanism. The alarm can be an acoustic, a visual or a tactile signal, or any combination thereof.

Preferably, the process comprises assembling a breathing activity sensor arranged to sense breathing of the patient into the induction device, configuring the processing unit to control the airflow generator to deliver air into the respiratory system of the patient according to a breathing scheme upon the breathing activity sensor failing to sense sufficient breathing of the patient, and optionally configuring the processing unit to control the induction device to activate the diaphragm in coordination with the breathing scheme upon the breathing activity sensor failing to sense sufficient breathing of the patient.

In a further other aspect, the invention is a method of ventilating a human or animal patient. This method comprises the steps of (i) connecting a conduit interface to a respiratory system of the human or animal patient; (ii) delivering air through the conduit interface into the respiratory system of the patient; (iii) controlling the delivery of air into the respiratory system of the patient according to a breathing scheme; and (iv) activating a diaphragm of the patient in coordination with the breathing scheme. The breathing scheme preferably comprises a time gap between start of operation of the induction device and start of operation of the air flow generator This ventilation method allows for efficiently achieving the effects and benefits described above in connection with the ventilation machine according to the invention and its preferred embodiments. In particular, advantageously the method is implemented by means of the ventilation machine according to the invention.

In the following further preferred steps and characteristics of the method according to the invention are listed.

Preferably, the method comprises a step of defining the breathing scheme in accordance with an intended therapy plan. Like this, the breathing scheme can be integrated in the therapy plan such that an improved therapy can be achieved.

Delivering air into the respiratory system of the patient according to the breathing scheme preferably comprises applying cycles of forwarding air into the respiratory system of the patient and allowing exhalation of air from the respiratory system. With such cycles, an efficient repetitive ventilation can be implemented.

Thereby, the diaphragm preferably is activated between the cycles of the breathing scheme. In particular, the diaphragm preferably is activated right before each start of one of the cycles of the breathing scheme.

Preferably, the induction device activates the diaphragm in synchrony with inhalation cycles of the breathing scheme.

Preferably, the air flow generator comprises an inspiration valve configured to allow delivery of air through the conduit interface into the respiratory system of the patient, and an expiration valve configured to allow patient exhalation, wherein, in accordance with the breathing scheme, the inspiration valve is synchronized with the activity of the induction device and the expiration valve is synchronized with inactivity of the induction device.

Preferably, activating the diaphragm of the patient in coordination with the breathing scheme comprises stimulating a Phrenic nerve. Thereby, the Phrenic nerve preferably is stimulated by a spatial electro-magnetic field having a targeted shape generated by a coil design. Such electromagnetic field allows for activating the diaphragm via the Phrenic nerve in an accurate and efficient manner.

Thereby, the method preferably comprises a step of holding the coil design at the patient. For example, for stimulating a Phrenic nerve, the coil design can be held at a neck of the patient.

Preferably, the method comprises a step of sensing for activation of the diaphragm.

Thereby, the method preferably comprises (i) automatically adjusting the position of the spatial electro-magnetic field generated by the coil design; (ii) automatically adjusting a field strength of the electro-magnetic field generated by the coil design; (iii) automatically varying the position of the spatial electro-magnetic field generated by the coil design of the induction device; automatically varying the field strength of the electro-magnetic field generated by the coil design of the induction device; (iv) receiving an activation feedback signal upon detection of an activation of the diaphragm; and (v) automatically stopping variation of the position of the spatial electro-magnetic field generated by the coil design of the induction device when the activation feedback signal is received and automatically stopping variation of the field strength of the electro-magnetic field generated by the coil design of the induction device when the activation feedback signal is received.

The step of sensing for activation of the diaphragm preferably comprises detecting an air flow change in the respiratory system of the patient induced by an activity of the diaphragm.

Preferably, the breathing scheme defines repetitively activating the diaphragm of the patient. Thereby, the repetitively activating the diaphragm of the patient preferably is ten to fifty stimulations per minute.

Preferably, activity of the induction device is stopped in synchrony with the end of each inhalation phase of the breathing cycles.

A sensor member preferably triggers the induction device and the air flow generator.

Thereby, the induction device and the air flow generator preferably are activated with an adjustable time gap towards the trigger from the sensor member.

Preferably, the induction device is triggered upon a signal characteristic of the sensor member measuring diaphragm activation and to trigger the air flow generator upon a signal characteristic from the sensor member measuring indirect diaphragm activation.

Preferably, plural breathing scheme parameters and/or field strength of the spatial electro-magnetic field and/or ramp duration of the spatial electro-magnetic field and/or overall air flow duration and/or flow field strengths and/or expiration phase duration are varied.

Preferably, the method comprises sensing spontaneous breathing of the patient, delivering air into the respiratory system of the patient according to a breathing scheme upon sensing spontaneous breathing of the patient fails, and activating the diaphragm in coordination with the breathing scheme upon sensing spontaneous breathing of the patient fails.

Within all aspects and embodiments of the invention involving the electro-magnetic field generator, the electro-magnetic field generator of all embodiments described herein advantageously is configured to provide pulses of electromagnetic fields, with adjustable field strength and frequency. Like this, convulsion of the patient or of specific body parts can be prevented. This can increase convenience and efficiency of the stimulation.

BRIEF DESCRIPTION OF THE DRAWINGS

The ventilation machine according to the invention as well as the process according to the invention and method according to the invention are described in more detail herein below by way of exemplary embodiments and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
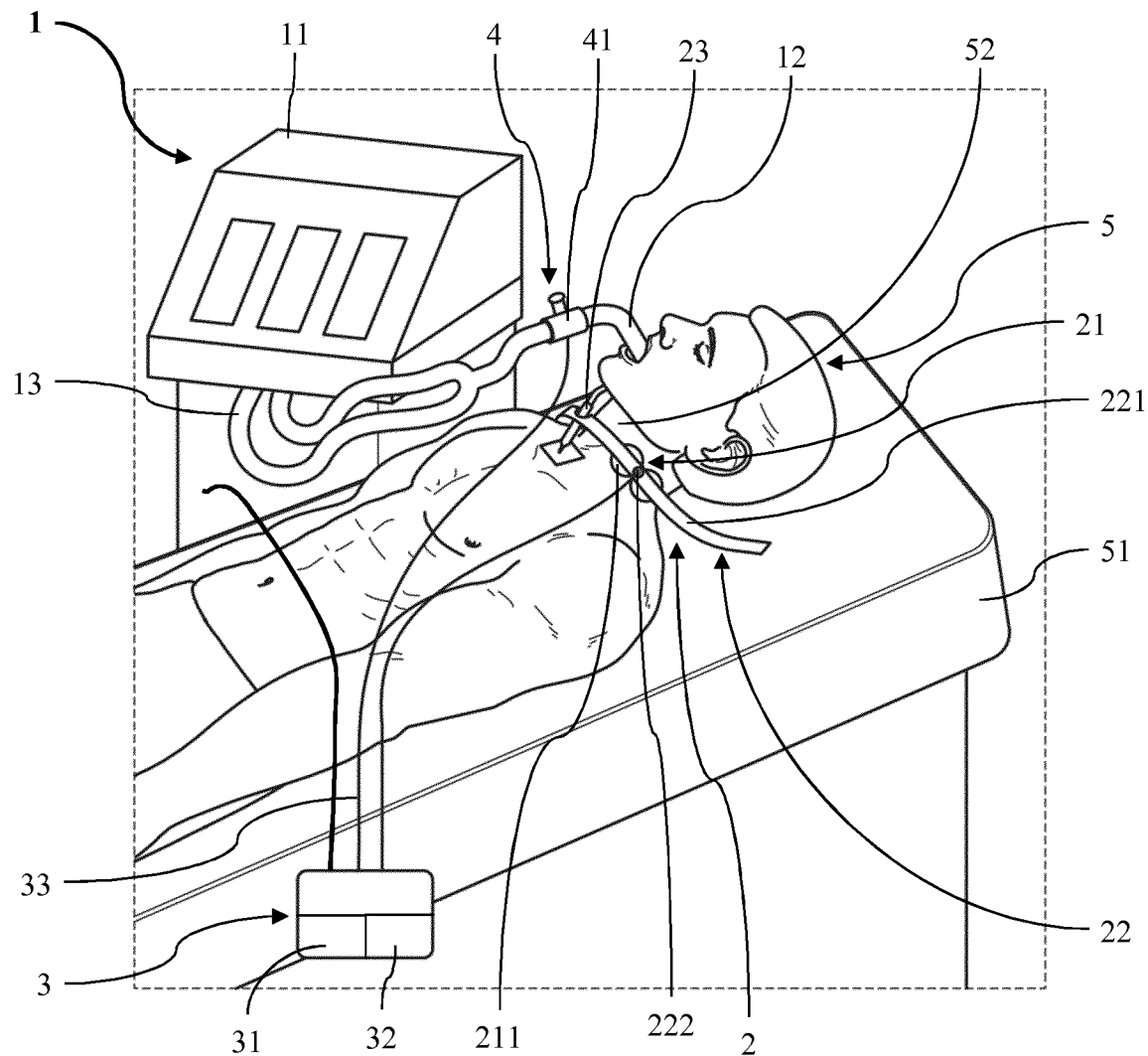
FIG. 1 shows a first embodiment of a ventilation machine according to the invention having a first variant of a electro-magnetic induction device.
Figure 3:
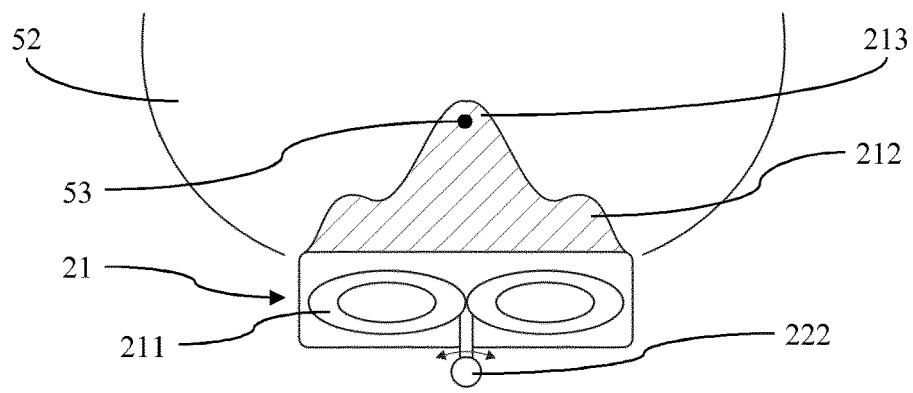
FIG. 3 shows an electro-magnetic field generated by the electro-magnetic induction device of FIG. 1.

FIG. 1 shows a first embodiment of a ventilation machine 1 according to the invention. The ventilation machine 1 has a first implementation an electro-magnetic induction device 2 (in the following also referred to as EMI device). The EMI device 2 comprises an electro-magnetic field generator 21 with two coils 211 as coil design. The coils 211 are located in one common plane and configured to generate a spatial electro-magnetic field 212. As can particularly be seen in FIG. 3, when operated, the two coils 211 generate the electro-magnetic field 212 towards a neck 52 of a patient 5. The electro-magnetic field 212 has a central targeted shape with a target area 213 at which the electro-magnetic field 212 maximally extends into the neck 52.

Turning back to FIG. 1, the EMI device 2 has a mounting arrangement 22 with a neck arc 221 arranged at the neck 52 of the patient 5 and fixed to a bed 51 the patient 5 lies on. The neck arc 221 is equipped with a joint 222 as repositioning structure of an electro-magnetic field adjustment mechanism of the EMI device 2. The joint 222 holds the coils 211 at the neck 52 of the patient 5.

The ventilation machine 1 further comprises a ventilator 11 as air flow generator from which ventilation tubes 13 extend. The ventilation machine 1 has a mouthpiece 12 as conduit interface of the ventilation machine 1 or as adapter of the EMI device. The mouthpiece 12 is applied to a mouth as entry point into the respiratory system of the patient 5. The ventilation tubes 13 are coupled to a flow sensor 41 of a sensor member 4 of the ventilation machine 1 or the EMI device 2.

The ventilation machine 1 further has a controller 3 as a processing unit with a calibration unit 31 and a field adjustment unit 32 of the electro-magnetic field adjustment mechanism. The controller 3 is in communication with the flow sensor 41, the ventilator 11 and the joint 222 via respective wires 33.

The calibration unit 31 is configured to manipulate the joint 222 to automatically vary the position of the target area 213 of the electro-magnetic field 212 generated by the coils 211 and the controller 3 to vary the field strength of the electro-magnetic field 212. The aim of varying field strength and position of the electro-magnetic filed 212 is to adjust the electro-magnetic field 212 such that it specifically stimulates a Phrenic nerve 53 of the patient 5 as can be best seen in FIG. 3. Upon stimulation of the Phrenic nerve 53, a diaphragm of the patient 5 is activated. Thereby, an airflow or breathing is induced which is sensed by the flow sensor 41.

The calibration unit 31 is configured to receive an activation feedback signal from the flow sensor 41 upon detection of activation of the diaphragm or upon detection of the airflow. Further, it is configured to stop variation of the position of the target area 213 of the electro-magnetic field 212 and the controller 3 to stop variation of the field strength of the electro-magnetic field 212 when the activation feedback is received.

The ventilator 11 is configured to deliver air through the mouthpiece 12 into the respiratory system of the patient 5. Thereby, the controller 3 is configured to control the ventilator 11 to deliver air into the respiratory system according to a breathing scheme defined in the controller 3. In particular, the controller 3 regulates the activation of the diaphragm in coordination with the breathing scheme such that activation of the diaphragm via the Phrenic nerve 53 is coordinated with the ventilation of the patient 5.

Figure 2:
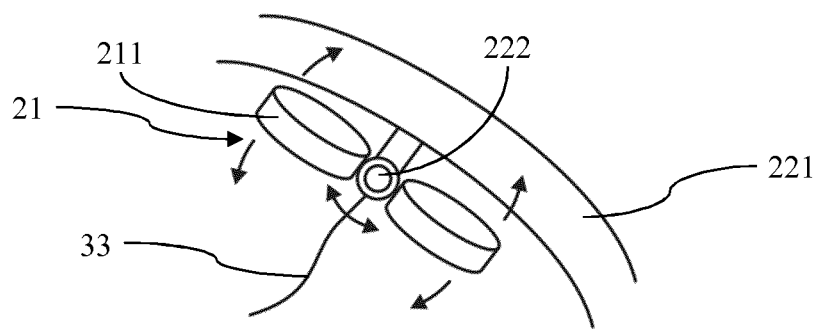
FIG. 2 shows an electro-magnetic field generator of the electro-magnetic induction device of FIG. 1.

In FIG. 2 the coils 211 of the electro-magnetic field generator 21 are shown on more detail. Thereby, it can be seen that the coils 211 are connected to the neck arc 221 via the joint 222. As indicated by the arrows in FIG. 2, the joint 222 can be tilted via the controller 3 such that also the coils 211 are commonly tilted or rotated. During calibration of the EMI device 2, the calibration unit 31 automatically tilts the coils 211 relative to the neck 52 of the patient 5 by moving the joint 222. Thereby, the electromagnetic field 212 and particularly its target area 213 is moved correspondingly. In addition to that, the calibration unit 31 varies the field strength of the electro-magnetic field 212 until the Phrenic nerve is in within the target area 213 and thereby stimulated.

The EMI device 2 is further equipped with a tracker 23 which is configured to detect a movement of the patient 5 relative to the coils 211 and to automatically induce a change of the position of the target area 213 of the electro-magnetic field 212 to compensate the detected movement of the patient 5. The tracker 23 is in communication with an alarm unit. It activates the alarm unit when the detected movement exceeds a range of compensation achievable by changing the position of the target area 213 of the electro-magnetic field 212.

The controller 3 is equipped with a wireless adapter to be connected to a mobile device such as a smartphone, tablet or the like as input interface. When the mobile device is connected, an operator can input an appropriate cyclic breathing scheme suitable for treating the patient 5. The breathing scheme is embodied such that the controller 3 induces operation in a predefined patient specific manner. Thereby, the ventilator 11 delivers air through the mouthpiece 12 into the respiratory system of the patient 5 by applying cycles of forwarding air into the respiratory system of the patient 5 and allowing exhalation of air from the respiratory system in accordance with the breathing scheme. Further, the EMI device 2 activates the diaphragm right before each start of one of the cycles of the breathing scheme.

Figure 4:
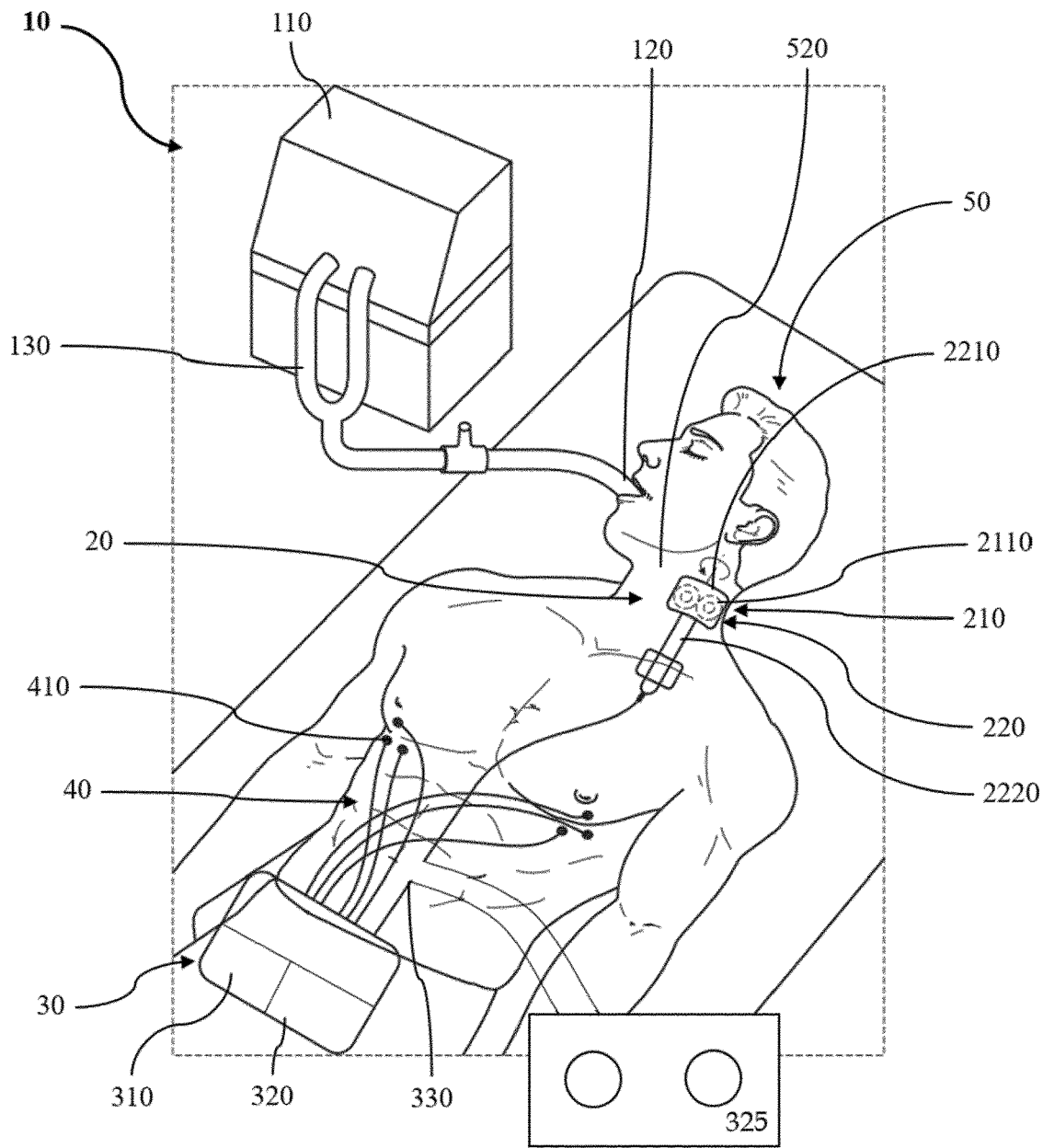
FIG. 4 shows a second embodiment of a ventilation machine according to the invention having a second variant of an electro-magnetic induction device.

FIG. 4 shows a second embodiment of a ventilation machine 10 according to the invention. It comprises a second implementation of an EMI device 20 which is equipped with an electro-magnetic field generator 210 with two coils 2110. The coils 2110 are configured to generate a spatial electro-magnetic field with a targeted shape. The EMI device 20 further has a mounting arrangement 220 with a tape 2210. The tape 2210 is provided with an adhesive and attached to a neck 520 of a patient 50.

The EMI device 20 is equipped with a shaft 2220 as repositionable element extending towards the coils 2110 and can tilt the electro-magnetic field around an axis of the shaft.

The ventilation machine 10 comprises a ventilator 110 as air flow generator from which ventilation tubes 130 extend. The EMI device 20 has a mouthpiece 120 as adapter or as conduit interface of the ventilation machine 10. The mouthpiece 120 is applied to a mouth as entry point into the respiratory system of the patient 50.

The ventilation machine 10 has a controller 30 as a processing unit with a calibration unit 310 and a field adjustment unit 320 of the electro-magnetic field adjustment mechanism. On the body of the patient 50 a plurality of electrodes 410 comprised by a sensor member 40 for detecting activation of the diaphragm. The controller 30 is in communication with the electrodes 410 and magnetic stimulator 325 which connects to the shaft 2220 via respective wires 330. The controller 30 further is wirelessly in communication with the ventilator 110.

The calibration unit 310 is configured to automatically vary the position of a spatial electro-magnetic field by automatically inducing the field adjustment unit 320 to reposition the shaft 2220 and by automatically varying the electro-magnetic field field strength. In particular, the shaft 2220 influences the alignment of the electromagnetic field around the axis of the shaft and thereby the location of the target area 213. Thus, by moving the shaft 2220, the targeted shape of the electro-magnetic field can be relocated. Like this, the spatial electro-magnetic field can be moved within the neck 520 of the patient 50. In particular, the calibration unit 310 is configured to vary the position of the spatial electro-magnetic field and to vary the field strength of the electro-magnetic field. Like this, the electro-magnetic field can be adjusted such that it specifically stimulates a Phrenic nerve of the patient 50. Upon stimulation of the Phrenic nerve, a diaphragm of the patient 50 is activated which is sensed by the electrodes 410.

The calibration unit 310 is configured to receive an activation feedback signal from the electrodes 410 upon detection of activation of the diaphragm. Further, it is configured to stop variation of the position of the spatial electro-magnetic field and to control the controller 30 to stop variation of the field strength of the electro-magnetic field when the activation feedback is received. The ventilator 110 is configured to deliver air through the mouthpiece 120 into the respiratory system of the patient 50. The controller 30 is configured to control the ventilator 110 such that its delivery of air into the respiratory system is in line with a breathing scheme defined in the controller 30. In particular, the controller 30 regulates the activation of the diaphragm in coordination with the breathing scheme such that activation of the diaphragm via the Phrenic nerve is coordinated with the ventilation and breathing of the patient 50.

The controller 30 is equipped with a wireless adapter to be connected to a mobile device such as a smartphone, tablet or the like as input interface. When the mobile device is connected, an operator can input an appropriate cyclic breathing scheme suitable for treating the patient 50. The breathing scheme is embodied such that the controller 30 induces ventilation and Phrenic nerve stimulation in a predefined and patient specific manner. Thereby, the ventilator 110 delivers air through the mouthpiece 120 into the respiratory system of the patient 50 by applying cycles of forwarding air into the respiratory system of the patient 50 and allowing exhalation of air from the respiratory system in accordance with the breathing scheme. Further, the EMI device 20 activates the diaphragm right before each start of one of the cycles of the breathing scheme.

Figure 5:
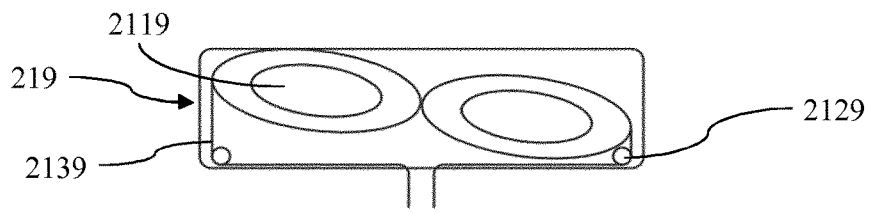
FIG. 5 shows an electro-magnetic field generator of a third variant of an electro-magnetic induction device in a tilted state.

In FIG. 5 an electro-magnetic field generator 219 of a third embodiment of an EMI device is shown. The electro-magnetic field generator 219 comprises a housing in which two coils 2119 are positioned. The coils 2119 are fixed to each other such that they can be moved or manipulated together as one unit. The coils 2119 are connected to cables 2139 at their lateral end sides. Starting from the coils 2119, the cables 2139 are redirected by respective pulleys 2129 and guided through an opening out of the housing.

Figure 6:
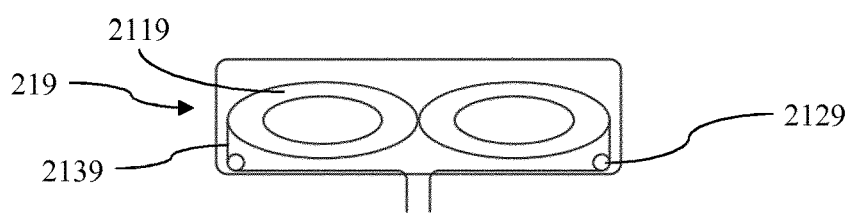
FIG. 6 shows the electro-magnetic field generator of FIG. 5 in an non-tilted state.

In FIG. 5 the coils 2119 are depicted in a tilted state in which the left coil 2119 is higher than the right coil 2119. For changing the tilting of the coils 2119, one of the cables 2139 can be pulled. As can be seen in FIG. 6, for moving the coils 2119 back to a straight position, the left cable 2139 is pulled such that the coils 2119 are rotated counter-clockwise.

Figure 7:
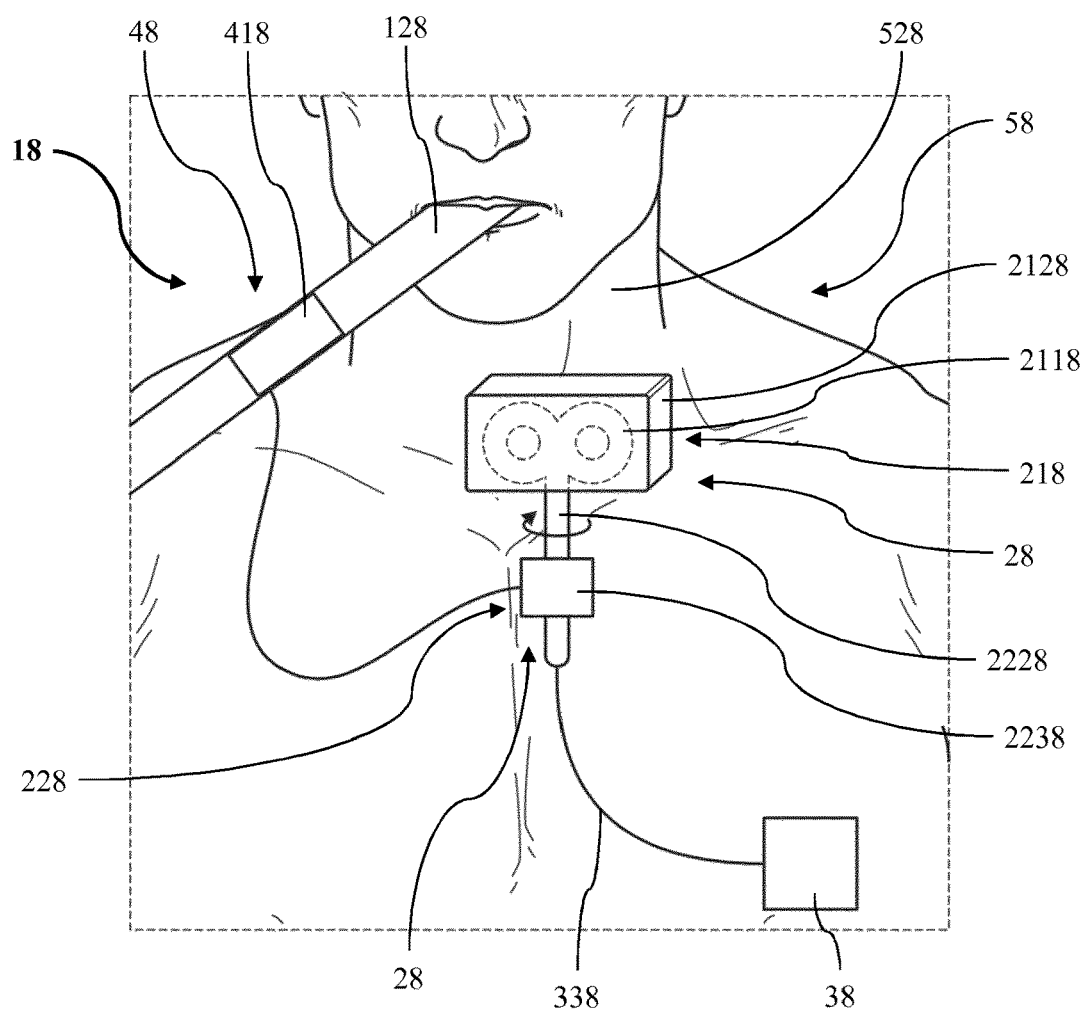
FIG. 7 shows a third embodiment of a ventilation machine according to the invention having a fourth variant of an electro-magnetic induction device.

FIG. 7 shows a third embodiment of a ventilation machine 18 according to the invention having a fourth embodiment of an EMI device 28. The EMI device 28 comprises an electro-magnetic field generator 218 with two coils 2118 as coil design. The electro-magnetic field generator 218 has a housing 2128 into which a shaft 2228 of a mounting arrangement 228 extends. The shaft 2228 is coupled to a shaft drive 2238 by which the shaft 2238 can be moved in the electro-magnetic field once created by the coils 2118.

The ventilation machine 18 comprises a ventilator as air flow generator from which ventilation tubes are connected to a mouthpiece 128 as conduit interface via a flow sensor 418 of a sensor member 48. The mouthpiece 128 is applied to a mouth of a patient 58 as entry point into his respiratory system.

The ventilation machine 18 has a controller 38 as a processing unit with a calibration unit and a field adjustment unit. The housing 2128 of the electro-magnetic field generator 218 the shaft drive 2238 and the controller 38 are attached to the patient 58 and, particularly, the electro-magnetic field generator 218 to his neck 528. Thereby, an adhesive of the mounting arrangement 228 is used. The controller 38 is in communication with the flow sensor 418 and the shaft drive 2238 by means of wires 338.

The ventilation apparatus 18 is correspondingly operated as the ventilation apparatus 10 described above in connection with FIG. 4.

Figure 8:
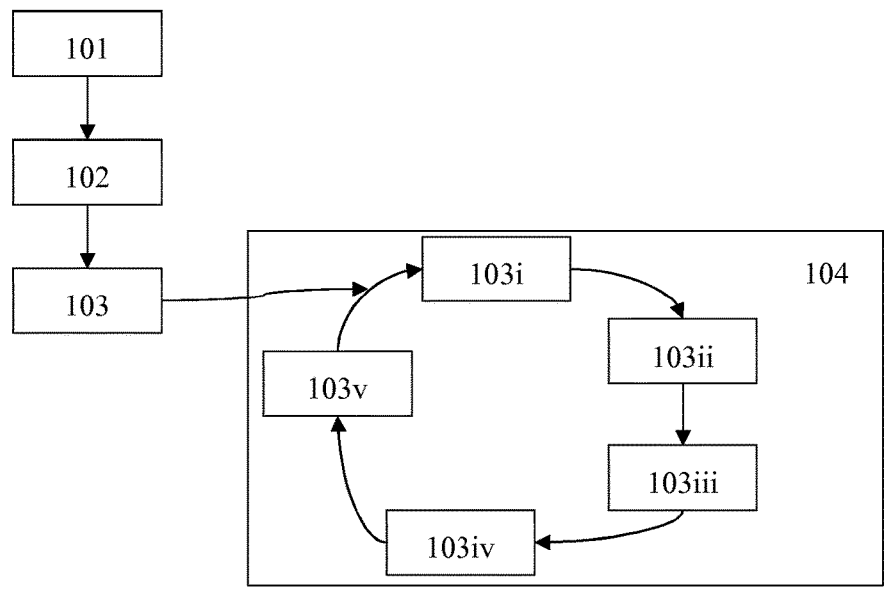
FIG. 8 shows a flow scheme of a first embodiment of a method of ventilating a human or animal patient according to the invention.

FIG. 8 shows an embodiment of a method of ventilating a human or animal patient according to the invention. The method involves any one of the ventilation machines described above or another embodiment of a ventilation machine according to the invention.

In a first step 101, a breathing scheme is defined by an operator. In particular, the operator defines the breathing scheme via a user interface provided by the ventilation machine. In a second step 102, a conduit interface of the ventilation machine is connected to a respiratory system of the patient. In particular, a mouthpiece of the conduit interface is mounted to a head of the patient such that nose and mouth are covered by the mouthpiece.

In a third step 103, air is delivered through the conduit interface into the respiratory system of the patient. More specifically, in sub-step 103*i* a flow sensor of the ventilating machine detects a spontaneous activity of the diaphragm by sensing an air flow inside the conduit interface. A first time gap predefined in the breathing scheme after such spontaneous activity is detected, in a sub-step 103*ii*, an electro-magnetic induction device of the ventilation machine stimulates the Phrenic nerve by applying a spatial electro-magnetic field. For such stimulation, a coil design of the electro-magnetic induction device, which is mounted to a neck of the patient, is energized. In particular, a train of electro-magnetic impulses is generated which are continuously increased in intensity until a target intensity is reached. Thereby, the diaphragm of the patient is activated. A second time gap predefined in the breathing scheme after such activation of the diaphragm, in a sub-step 103*iii*, an air flow generator of the ventilation machine delivers air through the conduit interface into the patient. In a sub-step 103*iv*, activation of the diaphragm as well as delivery of air is stopped and air is passively exhaled from the respiratory system of the patient. Then, in sub-step 103*v*, the ventilation is paused until in sub-step 103*i* the spontaneous activity is detected again.

The delivery of air into the respiratory system of the patient of step 103 is controlled by a processing unit of the ventilation machine in an ongoing or continuous step 104.

Figure 9:
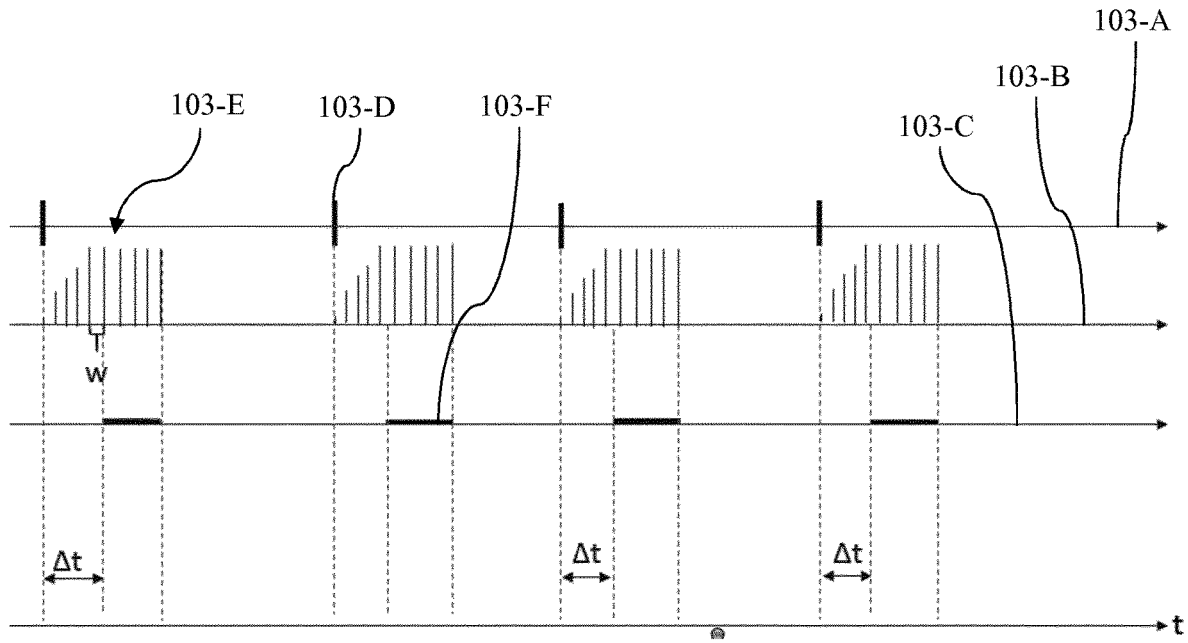
FIG. 9 shows a graphical representation of an exemplary breathing scheme defined in the method of FIG. 8.

In FIG. 9 a graph of the breathing scheme defined in step 101 of the method of FIG. 8 is shown. In this graph the bottom horizontal arrow represents time, the first horizontal arrow 103-A represents signals detected by the flow sensor, the second horizontal arrow 103-B represents the activity of an electro-magnetic induction device of the ventilation machine and the third horizontal arrow 103-C represents the activity of an air flow generator of the ventilation machine.

As can be seen in the graph of FIG. 9, the flow sensor detects a trigger event 103-D in the form of an air flow resulting from eventually weak spontaneous inhalation of the patient and transfers a respective signal to the processing unit of the ventilation machine. The processing unit then operates the electro-magnetic induction device such that it generates a spatial electro-magnetic field with a peak providing a train 103-E of electro-magnetic pulses. More specifically, the train 103-E comprise a number of electro-magnetic pulses which follow each other with a temporal width w, which can be in a range of about 33 milliseconds to about 66 milliseconds. Thereby, in the beginning of the train 103-E the intensity of the pulses stepwise increases until a target intensity is reached. Like this, impulses of the target intensity can smoothly be provided such that a resistance of the patient or discomfort can be decreased. The electro-magnetic induction device is mounted to a neck of the patient and adjusted to stimulate the Phrenic nerve. Thus, by providing the train 103-E the diaphragm of the patient is activated such it contracts and the patient inhales.

After the respective time gap Δt predefined in the breathing scheme, the processing unit operates the air flow generator such that an active air delivery 103-F into the respiratory system of the patient is provided via the conduit interface. During the air delivery 103-F the train 103-E is still provided such that in this phase inhalation is induced in parallel by the air flow generator and the electro-magnetic induction device. The flow sensor continuously senses the pressure and/or flow volume in the conduit interface. After the inhalation flow and/or pressure decreases a predefined threshold, the processing unit stops the air flow generator and the electro-magnetic induction device. Inhalation is then ended and the patient starts to spontaneously exhale. A further cycle then starts upon the flow sensor detecting a next trigger event 103-D.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below. For example, it is possible to operate the invention in embodiments with the following features:

During the complete application of the ventilation machine a base pressure can be applied by the air flow generator to the respiratory system of the patient.

The trigger event in the breathing scheme as starting point for the activation of the diaphragm can be provided by other means than the sensor member of the ventilation machine itself or a further sensor member. For example, a myogram can be used for detecting the trigger event.

The breathing scheme can define two different trigger events, one for inducing operation of the electro-magnetic induction device and one for inducing operation of the air flow generator. For example, the first trigger event can be based on a sensed activity of the diaphragm and the second trigger event based on a specific sensed flow and/or pressure.

The breathing scheme can define that operation of the air flow generator starts a predefined time after the electro-magnetic induction device. Or, it can start when a specific value is measured such as oxygen pressure in the blood or the like.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A ventilation machine comprising:
   a conduit interface configured to be connected to a respiratory system of a human or animal patient;
   an air flow generator configured to deliver air through the conduit interface into the respiratory system of the patient;
   a processing unit in communication with the air flow generator and configured to control the airflow generator to deliver air into the respiratory system of the patient according to a breathing scheme; and
   an induction device for activating a diaphragm of the patient, wherein
   the induction device is in communication with the processing unit, and
   the processing unit is configured to control the induction device to activate the diaphragm in coordination with the breathing scheme,
   wherein the induction device comprises an electro-magnetic field generator with a coil design configured to generate a spatial electro-magnetic field having a targeted shape, and
   wherein the electro-magnetic field is configured as a train of electro-magnetic pulses increasing in intensity until a target intensity is achieved to activate the diaphragm such that a continuous contraction or activation is induced.

2. The ventilation machine of claim 1, wherein the processing unit comprises an input interface and the processing unit is configured such that the breathing scheme can be inputted via the input interface.

3. The ventilation machine of claim 1, wherein the breathing scheme comprises a time gap between start of operation of the induction device and start of operation of the air flow generator.

4. The ventilation machine of claim 1, wherein the air flow generator is configured to deliver air through the conduit interface into the respiratory system of the patient by applying cycles of forwarding air into the respiratory system of the patient and allowing exhalation of air from the respiratory system in accordance with the breathing scheme.

5. The ventilation machine of claim 4, wherein the processing unit is configured to control the induction device to activate the diaphragm between the cycles of the breathing scheme.

6. The ventilation machine of claim 4, wherein the processing unit is configured to control the induction device to activate the diaphragm in synchrony with inhalation cycles of the breathing scheme.

7. The ventilation machine of claim 4, wherein the processing unit is configured to control the induction device to activate the diaphragm right before each start of one of the cycles of the breathing scheme.

8. The ventilation machine of claim 1, wherein the air flow generator comprises:
an inspiration valve configured to allow delivery of air through the conduit interface into the respiratory system of the patient, and
an expiration valve configured to allow patient exhalation, wherein, in accordance with the breathing scheme, the inspiration valve is synchronized with the activity of the induction device and the expiration valve is synchronized with inactivity of the induction device.

9. The ventilation machine of claim 1, wherein the induction device comprises:
at least one electrode configured to activate the diaphragm by transcutaneously stimulating a Phrenic nerve under control of the processing unit.

10. The ventilation machine of claim 1, wherein the induction device comprises:
a focused ultrasound device to activate the diaphragm by transcutaneously stimulating a Phrenic nerve under control of the processing unit, and/or
at least one electrode configured to activate the diaphragm percutaneously.

11. The ventilation machine of claim 1, wherein the processing unit is configured to stop activity of the induction device in synchrony with an end of each inhalation cycle of the breathing scheme.

12. The ventilation machine of claim 1, comprising a sensor member configured to detect an activation of the diaphragm.

13. The ventilation machine of claim 12, wherein the processing unit is configured:
to activate the induction device and the air flow generator with an adjustable time gap towards the trigger from the sensor member, and/or
to trigger the induction device upon a signal characteristic of the sensor member measuring diaphragm activation and to trigger the air flow generator upon a signal characteristic from the sensor member measuring indirect diaphragm activation, and/or
to automatically vary plural breathing scheme parameters and/or field strength of the spatial electro-magnetic field and/or ramp duration of the spatial electro-magnetic field and/or overall air flow duration and/or flow field strengths and/or expiration phase duration.

14. The ventilation machine of claim 12, comprising a calibration unit, wherein:
the induction device comprises an electro-magnetic field adjuster configured to automatically adjust the position of the spatial electro-magnetic field generated by the coil design,
the processing unit is in communication with the sensor member of the induction device and with the electro-magnetic field adjuster of the induction device,
the processing unit is configured to control the electro-magnetic field adjuster of the induction device to automatically vary the position of the spatial electro-magnetic field generated by the coil design of the induction device,
the processing unit is configured to receive an activation feedback signal from the sensor member of the induction device upon detection of the activation of the diaphragm, and
the processing unit is configured to control the electro-magnetic field adjuster of the induction device to automatically stop variation of the position of the spatial electro-magnetic field generated by the coil design of the induction.

15. The ventilation machine of claim 14, wherein the electro-magnetic field adjuster is configured to automatically adjust a field strength of the electro-magnetic field generated by the coil design, the processing unit is configured to control the electro-magnetic field adjuster of the induction device to automatically vary the field strength of the electro-magnetic field generated by the coil design of the induction device, and the processing unit is configured to control the electro-magnetic field adjuster of the induction device to automatically stop variation of the field strength of the electro-magnetic field generated by the coil design of the induction device.

16. The ventilation machine of claim 12, wherein the sensor member comprises:
a flow sensor connected to the conduit interface and configured to detect an air flow change induced by an activity of the diaphragm, and/or
a pressure sensor having an adaptor connectable to a respiratory system of the human or animal body, the pressure sensor being configured to detect a pressure change induced by an activity of the diaphragm.

17. The ventilation machine of claim 16, wherein the flow sensor of the sensor member is integral with the conduit interface.

18. The ventilation machine of claim 12, comprising a breathing activity sensor arranged to sense breathing of the patient, wherein the processing unit is configured to control the airflow generator to deliver air into the respiratory system of the patient according to a breathing scheme upon the breathing activity sensor failing to sense sufficient breathing of the patient, and optionally to control the induction device to activate the diaphragm in coordination with the breathing scheme upon the breathing activity sensor failing to sense sufficient breathing of the patient.

19. The ventilation machine of claim 12, wherein the sensor member is configured to trigger the induction device and the air flow generator.

20. A method of transcutaneous induction of a Phrenic nerve for a diagnostic purpose to assess diaphragm function, or sleep apnea, or other forms of sleep-disordered breathing, for repetitive regular transcutaneous induction of a Phrenic nerve for therapeutic use in patients with no spontaneous breath, for reanimation and keeping alive patient who have no function of a respiratory center, or for repeated transcutaneous induction of a Phrenic nerve for therapeutic use in patients with no or insufficient spontaneous diaphragm contractions who have at least a partly intact Phrenic nerve, by means of a ventilation machine according to claim 1.

21. The ventilation machine of claim 1, wherein the induction device is configured to activate the diaphragm by the spatial electro-magnetic field stimulating a Phrenic nerve under control of the processing unit and/or wherein the induction device comprises a mount holding the coil design of the electro-magnetic field generator, the mount being configured to hold the coil design of the electro-magnetic field generator at the patient.

22. A process of manufacturing a ventilation machine comprising:
    assembling to the ventilation machine
        a conduit interface configured to be connected to a respiratory system of a human or animal patient,
        an air flow generator configured to deliver air through the conduit interface into the respiratory system of the patient,
        a processing unit in communication with the air flow generator and configured to control the airflow generator to deliver air into the respiratory system of the patient according to a breathing scheme, and
        an induction device for activating a diaphragm of the patient, wherein the induction device is in communication with the processing unit;
    configuring the processing unit to control the induction device to activate the diaphragm in coordination with the breathing scheme;
    providing the induction device with an electro-magnetic field generator with a coil design; and
    configuring the coil design to generate a spatial electro-magnetic field having a targeted shape, wherein the electro-magnetic field is a train of electro-magnetic pulses that are continuously increased in intensity until a target intensity is achieved to activate the diaphragm such that a continuous contraction or activation is induced.

23. The process of claim 22, wherein the breathing scheme comprises a time gap between start of operation of the induction device and start of operation of the air flow generator.

24. The process of claim 22, comprising:
    providing the processing unit with an input interface and the processing unit is configured such that the breathing scheme can be inputted via the input interface, and/or
    configuring the air flow generator to deliver air through the conduit interface into the respiratory system of the patient by applying cycles of forwarding air into the respiratory system of the patient and allowing exhalation of air from the respiratory system in accordance with the breathing scheme.

25. The process of claim 24, comprising:
    configuring the processing unit to control the induction device to activate the diaphragm between the cycles of the breathing scheme, and/or
    configuring the processing unit to control the induction device to activate the diaphragm right before each start of one of the cycles of the breathing scheme.

26. The process of claim 22, wherein:
    the processing unit is configured to control the induction device to activate the diaphragm in synchrony with inhalation cycles of the breathing scheme, and/or
    the air flow generator comprises an inspiration valve configured to allow delivery of air through the conduit interface into the respiratory system of the patient, and an expiration valve configured to allow patient exhalation,
    wherein, in accordance with the breathing scheme, the inspiration valve is synchronized with the activity of the induction device and the expiration valve is synchronized with inactivity of the induction device.

27. The process of claim 22, comprising:
    providing the induction device with at least one electrode configured to activate the diaphragm by transcutaneously stimulating a Phrenic nerve under control of the processing unit, and/or
    configuring the induction device to activate the diaphragm by the spatial electro-magnetic field stimulating a Phrenic nerve under control of the processing unit.

28. The process of claim 27, comprising providing the induction device with a mount holding the coil design of the electro-magnetic field generator, and configuring the mount to hold the coil design of the electro-magnetic field generator at the patient.

29. The process of claim 22, comprising:
    configuring the processing unit to stop activity of the induction device in synchrony with an end of each inhalation cycle of the breathing scheme, and/or
    providing the ventilation machine with a sensor member configured to detect an activation of the diaphragm.

30. The process of claim 29, comprising configuring the processing unit:
    to activate the induction device and the air flow generator with an adjustable time gap towards the trigger from the sensor member, and/or
    to trigger the induction device upon a signal characteristic of the sensor member measuring diaphragm activation and to trigger the air flow generator upon a signal characteristic from the sensor member measuring indirect diaphragm activation, and/or
    to automatically vary plural breathing scheme parameters and/or field strength of the spatial electro-magnetic field and/or ramp duration of the spatial electro-magnetic field and/or overall air flow duration and/or flow field strengths and/or expiration phase duration and/or temporal characteristics of the electro-magnetic field.

31. The process of claim 29, comprising providing the ventilation machine with a calibration unit, wherein:
    the induction device is provided with an electro-magnetic field adjuster configured to automatically adjust the position of the spatial electro-magnetic field generated by the coil design and optionally to automatically adjust a field strength of the electro-magnetic field generated by the coil design,
    the processing unit is in communication with the sensor member of the induction device and with the electro-magnetic field adjuster of the induction device,
    the processing unit is configured to control the electro-magnetic field adjuster of the induction device to automatically vary the position of the spatial electro-magnetic field generated by the coil design of the induction device and optionally to automatically vary the field strength of the electro-magnetic field generated by the coil design of the induction device,
    the processing unit is configured to receive an activation feedback signal from the sensor member of the induction device upon detection of the activation of the diaphragm, and
    the processing unit is configured to control the electro-magnetic field adjuster of the induction device to automatically stop variation of the position of the spatial electro-magnetic field generated by the coil design of the induction device and optionally to automatically stop variation of the field strength of the electro-magnetic field generated by the coil design of the induction device.

32. The process of claim 31, comprising providing the sensor member with a flow sensor connected to the conduit interface and configured to detect an air flow change induced by an activity of the diaphragm.

33. The process of claim 32, wherein the flow sensor of the sensor member is integral with the conduit interface.

34. The process of claim 31, comprising:
assembling an alarm unit into the induction device, wherein a tracker is connected to the alarm unit and configured to activate the alarm unit when a movement of the patient detected by the tracker exceeds a range of compensation achievable by changing the position of the spatial electro-magnetic field generated by the coil design via the electro-magnetic field adjuster.

35. The process of claim 29, wherein the sensor member is configured to trigger the induction device and the air flow generator.

36. The process of claim 22, comprising:
assembling a breathing activity sensor arranged to sense breathing of the patient into the induction device, configuring the processing unit to control the airflow generator to deliver air into the respiratory system of the patient according to a breathing scheme upon the breathing activity sensor failing to sense sufficient breathing of the patient, and optionally configuring the processing unit to control the induction device to activate the diaphragm in coordination with the breathing scheme upon the breathing activity sensor failing to sense sufficient breathing of the patient.

37. A method of ventilating a human or animal patient comprising:
connecting a conduit interface to a respiratory system of the human or animal patient;
delivering air through the conduit interface into the respiratory system of the patient;
controlling the delivery of air into the respiratory system of the patient according to a breathing scheme; and
activating a diaphragm of the patient by an induction device in coordination with the breathing scheme,
wherein the induction device comprises an electro-magnetic field generator,
wherein activating a diaphragm of the patient in coordination with the breathing scheme comprises stimulating a Phrenic nerve, and
wherein the Phrenic nerve is stimulated by a spatial electro-magnetic field having a targeted shape generated by a coil design of the electro-magnetic field generator, wherein the electro-magnetic field is a train of electro-magnetic pulses that are continuously increased in intensity until a target intensity is achieved to activate the diaphragm such that a continuous contraction or activation is induced.

38. The method of claim 37, wherein the breathing scheme comprises a time gap between start of operation of the induction device and start of operation of the air flow generator.

39. The method of claim 37, comprising defining the breathing scheme in accordance with an intended therapy plan.

40. The method of claim 37, wherein the delivering air into the respiratory system of the patient according to the breathing scheme comprises applying cycles of forwarding air into the respiratory system of the patient and allowing exhalation of air from the respiratory system.

41. The method of claim 40, wherein the diaphragm is activated between the cycles of the breathing scheme, and/or wherein the diaphragm is activated right before each start of one of the cycles of the breathing scheme.

42. The method of claim 37, wherein the induction device activates the diaphragm in synchrony with inhalation cycles of the breathing scheme.

43. The method of claim 37, wherein the air flow generator comprises an inspiration valve configured to allow delivery of air through the conduit interface into the respiratory system of the patient, and an expiration valve configured to allow patient exhalation, wherein, in accordance with the breathing scheme, the inspiration valve is synchronized with the activity of the induction device and the expiration valve is synchronized with inactivity of the induction device.

44. The method of claim 37, wherein the coil design preferably is held at the patient.

45. The method of claim 44, comprising:
automatically adjusting the position of the spatial electro-magnetic field generated by the coil design,
automatically adjusting a field strength of the electro-magnetic field generated by the coil design,
automatically varying the position of the spatial electro-magnetic field generated by the coil design of the induction device,
automatically varying the field strength of the electro-magnetic field generated by the coil design of the induction device,
receiving an activation feedback signal upon detection of an activation of the diaphragm, and
automatically stopping variation of the position of the spatial electro-magnetic field generated by the coil design of the induction device when the activation feedback signal is received and automatically stopping variation of the field strength of the electro-magnetic field generated by the coil design of the induction device when the activation feedback signal is received.

46. The method of claim 37, comprising sensing for activation of the diaphragm.

47. The method of claim 46, wherein sensing for activation of the diaphragm comprises detecting an air flow change in the respiratory system of the patient induced by an activity of the diaphragm.

48. The method of claim 37, wherein the breathing scheme defines repetitively activating the diaphragm of the patient.

49. The method of claim 48, wherein the repetitively activating the diaphragm of the patient is ten to fifty stimulations per minute.

50. The method of claim 37, wherein activity of the induction device is stopped in synchrony with an end of each inhalation cycle of the breathing scheme.

51. The method of claim 37, wherein a sensor member triggers the induction device and the air flow generator.

52. The method of claim 51, wherein the induction device and the air flow generator are activated with an adjustable time gap towards the trigger from the sensor member, and/or wherein the induction device is triggered upon a signal characteristic of the sensor member measuring diaphragm activation and to trigger the air flow generator upon a signal characteristic from the sensor member measuring indirect diaphragm activation.

53. The method of claim 37, wherein plural breathing scheme parameters and/or field strength of the spatial electro-magnetic field and/or ramp duration of the spatial electro-magnetic field and/or overall air flow duration and/or flow field strengths and/or expiration phase duration temporal characteristics of the electro-magnetic field are varied.

54. The method of claim 37, comprising sensing breathing of the patient, delivering air into the respiratory system of the patient according to a breathing scheme upon sensing sufficient breathing of the patient fails, and optionally-activating the diaphragm in coordination with the breathing scheme upon sensing sufficient breathing of the patient fails.

* * * * *